United States Patent
Medeiros

(10) Patent No.: US 11,839,446 B2
(45) Date of Patent: Dec. 12, 2023

(54) WIRELESS PATIENT MONITORING SYSTEM AND METHOD

(71) Applicant: GE Precision Healthcare LLC, Wauwatosa, WI (US)

(72) Inventor: Daniel W. Medeiros, Wauwatosa, WI (US)

(73) Assignee: GE Precision Healthcare LLC, Wauwatosa, WI (US)

(*) Notice: Subject to any disclaimer, the term of this patent is extended or adjusted under 35 U.S.C. 154(b) by 276 days.

(21) Appl. No.: 16/890,829

(22) Filed: Jun. 2, 2020

(65) Prior Publication Data

US 2021/0369116 A1 Dec. 2, 2021

(51) Int. Cl.
*A61B 5/00* (2006.01)
*A61B 5/0205* (2006.01)

(52) U.S. Cl.
CPC ........ *A61B 5/0024* (2013.01); *A61B 5/02055* (2013.01); *A61B 5/6801* (2013.01); *A61B 5/746* (2013.01)

(58) Field of Classification Search
CPC ... A61B 5/0002; A61B 5/0004; A61B 5/0006; A61B 5/0008; A61B 5/0015; A61B 5/0022; A61B 5/0024; A61B 5/0026; A61B 5/02; A61B 5/02055; A61B 5/6801; A61B 5/746; H04Q 9/00; H04Q 2209/00; H04Q 2209/10; H04Q 2209/40; H04Q 2209/43; H04Q 2209/70; H04Q 2209/80; H04Q 2209/82; H04Q 2209/823; H04Q 2209/826; H04Q 2209/84
See application file for complete search history.

(56) References Cited

U.S. PATENT DOCUMENTS

| | | | |
|---|---|---|---|
| 6,513,723 B1* | 2/2003 | Mueller | F23N 5/022 236/51 |
| 8,136,395 B2* | 3/2012 | Pop | E21B 49/008 73/152.51 |
| 10,274,325 B2* | 4/2019 | Rombouts | G05D 1/0274 |
| 11,229,382 B2* | 1/2022 | Feldman | A61B 5/6833 |
| 2014/0187890 A1* | 7/2014 | Mensinger | A61B 5/14532 600/365 |
| 2020/0137658 A1* | 4/2020 | Gattu | H04W 52/0251 |

* cited by examiner

*Primary Examiner* — Franklin D Balseca
(74) *Attorney, Agent, or Firm* — ANDRUS INTELLECTUAL PROPERTY LAW, LLP

(57) ABSTRACT

A wireless patient monitoring system includes at least one wireless physiological sensor having a sensing element senses physiological parameter information from a patient. A sensor controller is configured to determine a current parameter value based on the physiological parameter information and to compare the current parameter value to a prior parameter value. Based on the comparison, the sensor controller determines if the current parameter value is redundant of the prior parameter value. If so, then the current parameter value is not transmitted. If the current parameter is not redundant of the prior parameter value, then a wireless transmitter is controlled to wirelessly transmit the current parameter value.

18 Claims, 5 Drawing Sheets

WIRELESS PATIENT MONITORING SYSTEM AND METHOD

BACKGROUND

The present disclosure relates generally to patient monitoring devices and systems for monitoring a patient's physiology and health status. More specifically, the present disclosure relates to patient monitoring devices, systems, and methods that wirelessly transmit patient physiological data.

In the field of medicine, physicians often desire to monitor multiple physiological characteristics of their patients. Oftentimes, patient monitoring involves the use of several separate monitoring devices simultaneously, such as an electrocardiograph (ECG), a pulse oximeter, a respiration monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged into a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. However, patients that are not being regularly monitored may encounter risky health situations that that go undetected for a period of time, such as where rapid changes occur in physiological parameters that are not checked by a clinician until hours later or until a critical situation occurs. Thus, it is often desirable to continually or frequently obtain certain physiological information from a patient, which is a battery-intensive endeavor.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a wireless patient monitoring system includes at least one wireless physiological sensor having a sensing element senses physiological parameter information from a patient. A sensor controller is configured to determine a current parameter value based on the physiological parameter information and to compare the current parameter value to a prior parameter value. Based on the comparison, the sensor controller determines if the current parameter value is redundant of the prior parameter value. If so, then the current parameter value is not transmitted. If the current parameter is not redundant of the prior parameter value, then a wireless transmitter is controlled to wirelessly transmit the current parameter value.

One embodiment of a method of physiological monitoring includes sensing physiological parameter information from a patient with a sensing element in a wireless physiological sensor and determining a current parameter value based on the physiological parameter information. The current parameter value is then compared to a prior parameter value to determine if the current parameter value is redundant of the prior parameter value. If the current parameter is not redundant of the prior parameter value, then a wireless transmitter is operated to wirelessly transmit the current parameter value. If the current parameter value is redundant of the prior parameter value, then the current parameter value is not transmitted.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventor has recognized that wireless monitoring systems are desirable, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventor has recognized that an important aspect of decreasing the size and weight of wireless physiological sensors is decreasing battery size, and that a major challenge in the development of wireless physiological sensors has been the conflicting demands of constant monitoring and high power consumption and the requirement for long battery life.

The inventor has recognized that data transmission plays a significant role in battery consumption and that, for many types of wireless physiological sensors, transmitting data is the most power-consuming activity performed by the sensor. In view of the foregoing problems and challenges in the relevant art, the inventor has developed the disclosed system where battery life is conserved by not transmitting redundant physiological data where a current physiological value or measurement is materially equal to a value that has already been transmitted. Thereby, power consumption of the wireless sensor is reduced and battery life is extended without reducing the fidelity of physiological monitoring.

Figure 1:
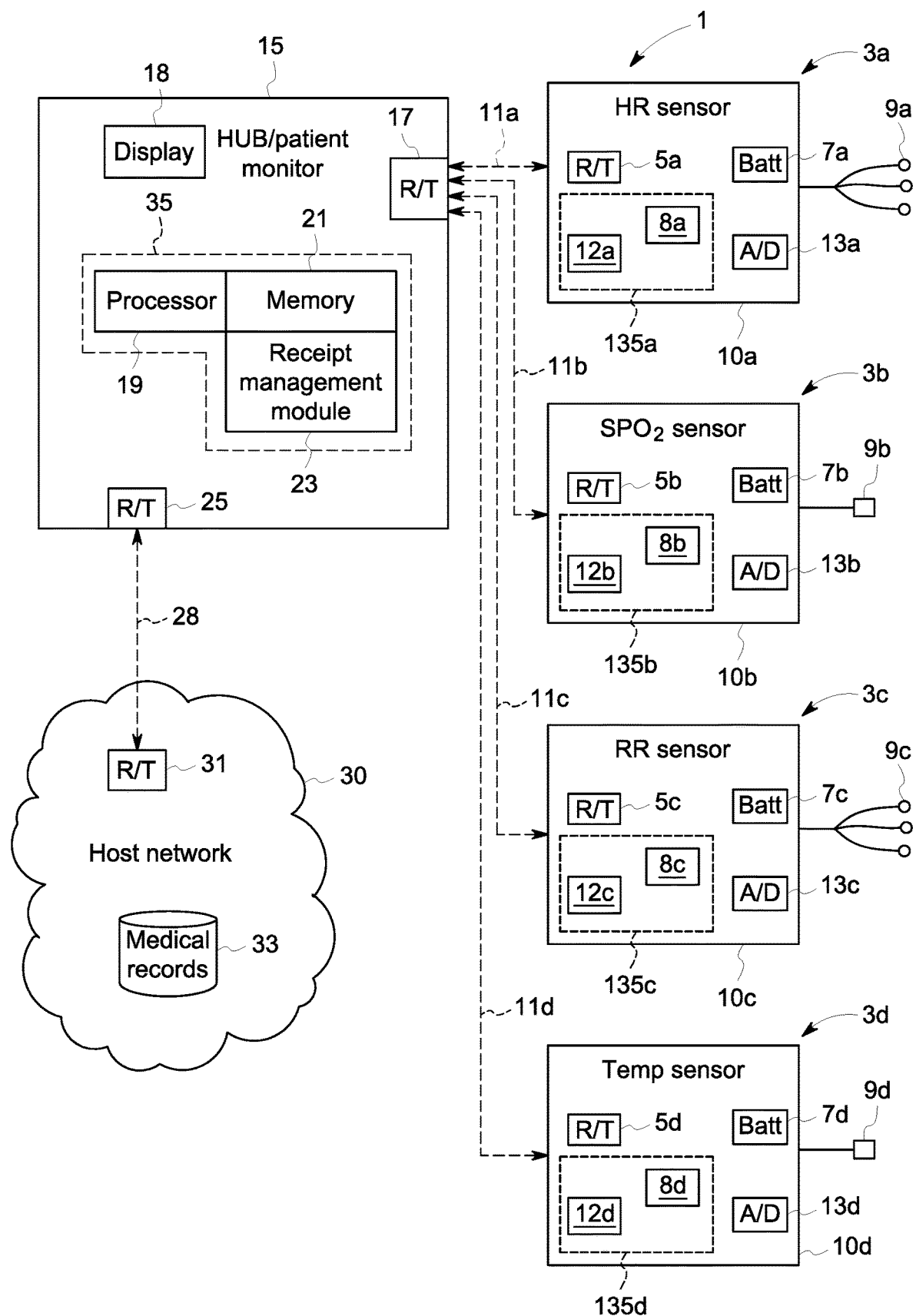
FIG. 1 is a schematic diagram of a wireless patient monitoring system according to one embodiment of the present disclosure.

FIG. 1 depicts one embodiment of a patient monitoring system 1 containing four wireless physiological sensors 3a-3d in wireless communication with a hub 15, which may be for example a patient monitor. The hub 15 is in wireless communication with a host network 30 that contains medical records database 33. For example, the hub 15 may be attached to the patient's body, placed on or near the patient's bed, integrated into another patient care device (such as an incubator housing a monitored neonate, an anesthesia machine connected to the monitored patient, etc.). The hub 15 may be positioned within range of the patient, such as in the same room as the patient. The hub 15 may be a separate, stand-alone device, or it may be incorporated and/or housed with another device within the system 1, such as housed with one of the wireless sensing devices 3a-3d. Each wireless physiological sensor 3a-3d includes one or more sensing elements 9a-9d for measuring physiological information from a patient, and also includes a base unit 10a-10d that receives the physiological information from the sensing elements 9a-9d and transmits a parameter dataset based on those measurements to the hub device 15 via a respective communication link 11a-11d.

The sensing elements 9a-9d may be connected to the respective base unit 10a-10d by wired or wireless means. The sensing elements 9a-9d may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like.

In various depicted embodiments, wireless sensing devices measuring different physiological parameters may be networked to the hub 15 as shown in FIG. 1 that communicates with a central, host network 30, such as a central network of a medical facility. In another embodiment, the wireless sensing devices may communicate directly with the host network 30, and such and embodiment is within the scope of the present disclosure. The data transmission methods and systems described herein may be utilized for transmission of patient data by and between one or more of the wireless physiological sensors 3, hub 15, and/or host network 30.

In the depicted embodiment, a first wireless physiological sensor 3a is a heart rate sensing device having sensing element 9a configured to sense heart rate. In one embodiment, this may be a pulse sensor, in another embodiment the heart rate may be detected via ECG monitoring techniques and thus the sensing element 9a may be two or more ECG electrodes. A second wireless physiological sensor 3b is a peripheral oxygen saturation (SpO2) sensing device having a sensing element 9b that is a pulse oximetry sensor, such as a standard infrared pulse oximetry sensor configured for placement on a patient's fingertip. A third wireless physiological sensor 3c is a respiration rate sensing device having sensing elements 9c that is a respiration sensor, examples of which are well-known in the art. A fourth wireless physiological sensor 3d is a temperature sensor having sensing elements 9d that measures a patient's temperature, such as a skin temperature sensor. It should be understood that the patient monitoring system 1 of the present disclosure is not limited to the examples of sensor devices provided, but may be configured and employed to sense and monitor any clinical parameter. Likewise, the monitoring system 1 may be a multi-parameter system, or may only include one wireless physiological sensor 3. The examples provided herein are for the purposes of demonstrating the invention and should not be considered limiting.

The base units 10a-10c of each of the exemplary wireless physiological sensors 3a-3d include analog-to-digital (A/D) converters 13a-13d, which may be any devices or logic sets capable of digitizing analog physiological signals or physiological information recorded by the associated sensors 9a-9d. For example, the A/D converters 13a-13d may be Analog Front End (AFE) devices. The base units 10a-10d may each include a controller 135a-135d. Each controller may comprise a processor 12a-12d that receives the digital physiological data and determines whether to the data is redundant of previously-transmitted data or is not redundant of the previously-transmitted data. In certain embodiments, the controller 135a-135d determines a current parameter value based on received physiological data, such as a current heart rate, a current SpO$_2$, a current respiration rate, or a current temperature. The controller 135a-135d then determines whether the respective current parameter value is redundant of a prior value to assess whether transmission should be effectuated.

Each base unit 10a-10c may be configured differently depending on the type of wireless physiological sensor, and may be configured to perform various signal processing functions and or sensor control functions. To provide just a few examples, the processor 12a in the ECG physiological sensor 3a may be configured to filter the digital signal from the ECG sensing elements 9a to remove artifact and/or to perform various calculations and determinations based on the recorded cardiac data, such as heart rate. Each wireless physiological sensor 3a-3d includes a battery 7a-7d that stores energy and powers the various aspects thereof. Each controller 135a-135d may further include power management capabilities, especially where the respective wireless physiological sensor 3a-3d contains more demanding electrical or electromechanical aspects.

In other embodiments, the controller 135a-135d may not perform any signal processing tasks and may simply be configured to perform necessary control functions for the respective wireless physiological sensor 3a-3d. In such an embodiment, the data to be transmitted only includes the digitized raw data or digitized filtered data from the various sensing elements 9a-9d.

The data is then transmitted according to the methods described herein. For example, each physiological sensor 3a-3d may contain a transmission management module 8a-8d that is a set of software instructions executable within the controller 135a-135d of the respective physiological sensor 3a-3d to determine whether the current parameter value or parameter data should be transmitted, or is redundant and transmission is unnecessary. This process is described in more detail and exemplified below.

The receiver/transmitter 5a-5d of each wireless physiological sensor 3a-3d communicates via the respective communication link 11a-11d with the receiver/transmitter 17 of the hub 15, which may each include separate receiving and transmitting devices or may include an integrated device providing both functions, such as a transceiver. The receiver/transmitters 5a-5d of the wireless physiological sensors 3a-3d and the receiver/transmitter 17 of the hub 15 may communicate by any radio frequency standard known in the art for wirelessly transmitting data between two points. In one embodiment, the receiver/transmitters 5a-5d and 17 may operate as body area network (BAN) devices, such as medical body area network (MBAN) devices, that operate as a wireless network. For example, the wireless physiological sensors 3a-3d may be wearable or portable computing devices in communication with a hub 15 positioned in appropriate proximity of the patient. Other examples of radio protocols that could be used for this purpose include, but are not limited to, Wi-Fi, Bluetooth, Bluetooth Low Energy (BLE), ANT, IEEE 802.15.4 (e.g., Zigbee or 6LoW-PAN).

The hub 15 may then communicate with a host network 30 via a wireless communication link 28, such as to transmit the data from the respective wireless physiological sensor 3a-3d to the host network 30 for display and/or for storage in the patient's medical record. In certain embodiments, the hub 15 may be configured to act as a patient monitor and to receive the current parameter value from the wireless physiological sensor 3a-3d and to assess the patient's physiological condition based thereon. The hub 15 may also be configured to monitor the performance and transmission of the sensor 3a-3d and to make sure that the sensor transmits physiological data with sufficient frequency, examples of which are described below.

The hub 15 has receiver/transmitter 25 that communicates with a receiver/transmitter 31 associated with the host network 30 on communication link 28, which may operate according to a network protocol appropriate for longer-range wireless transmissions, such as on the wireless medical telemetry service (WMTS) spectrum or on a Wi-Fi-compliant wireless local area network (LAN). The host network 30 may be, for example, a local computer network having servers housed within a medical facility treating the patient, or it may be a cloud-based system hosted by a cloud computing provider. The host network 30 may include a medical records database 33 housing the medical records for the patient, which may be updated to store the parameter datasets recorded and transmitted by the various wireless sensors 3a-3d. As described above, other embodiments may be arranged such that one or more of the sensors 3a-3d may transmit directly to the host network 30 and the host network 30 may perform any or all of the functions just described and attributed to the hub 15.

Figure 2:
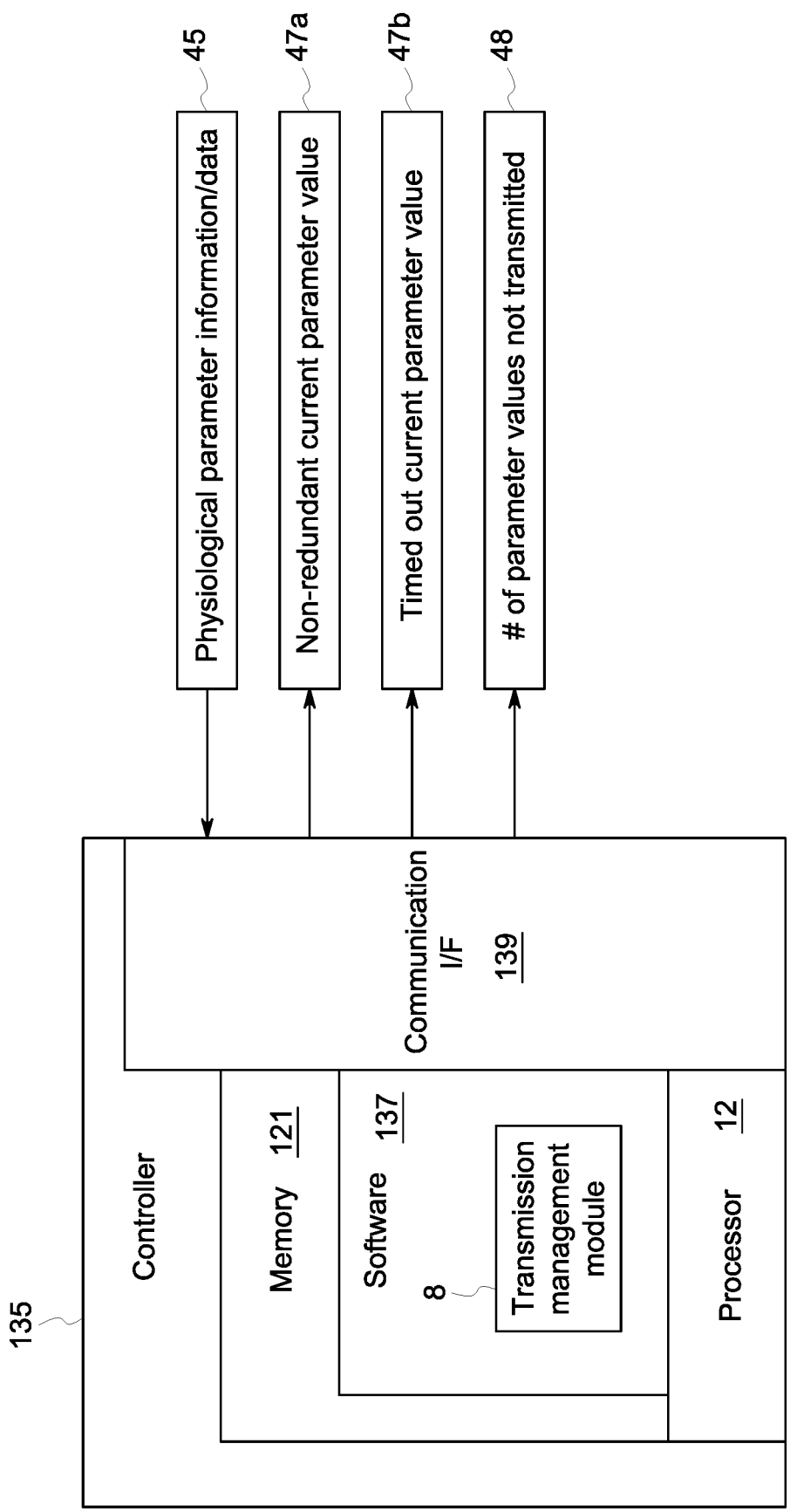
FIG. 2 depicts a controller and logic of an exemplary wireless sensor according to the present disclosure.

FIG. 2 provides a system diagram of a controller 135 (e.g. each of the controllers 135a-135D in each sensor 3a-3d) having a transmission management module 8 being software executable to assess redundancy and whether current parameter values should be transmitted. The controller 135 includes a processor 12, memory 121, software 137 (which includes the transmission management module 8 and other software for executing the various data processing and data transmission functions of the sensor), and communication interface 139. The processor 19 loads and executes software 37 from memory 21, including the transmission management module 8, which is an application within the software 37. Each transmission management module 8 includes computer-readable instructions that, when executed by the controller 135 (including the processor 19), direct the operation as described herein. Although the controller 135 as depicted in FIG. 3 includes one software element 137 encapsulating one transmission management module 8, it should be understood that one or more software elements having one or more modules may provide the same operation.

As illustrated in FIG. 2, the controller 135 is configured to receive physiological parameter information 45, which may be digitized data, and to assess whether such information should be transmitted. The controller 135 may determine a discrete value based on the physiological parameter information 45. For instance, the monitored parameter value may be heart rate, respiration rate, SpO2, or temperature. The controller 135 then determines whether the current parameter value 47 is redundant of a prior parameter value. Non-redundant current parameter values 47a are transmitted to the hub 15. If the current parameter value 47 is redundant of the prior parameter value, then it is not transmitted. However, in certain embodiments, the controller 135 may be configured to determine a time out value or threshold number of untransmitted parameter values, and to transmit the current parameter value regardless of redundancy once the timeout threshold time is reached (i.e., the timed out current parameter value 47b). In certain embodiments, the controller 135 may further be configured to transmit information regarding the number of redundant parameter values that were not transmitted, such as a number of parameters values not transmitted 48 and/or information regarding the amount of time between transmissions.

In other embodiments, the hub 15 or other receiving system or device, such as the host network 30, may be configured to track a period of time since a last received parameter value. This time monitoring by the receiving device may be an alternative to or in addition to the count of time monitoring by the sensor 3. In certain embodiments, if the period of time since the last received parameter value at the hub 15 or host network 30 exceeds a timeout value, the hub 15 and/or host network 30 may be configured to prompt the wireless physiological sensor 3 to transmit the current parameter value. In certain embodiments, the hub 15 and/or host network 30 may be configured to generate an alert if the period of time since the last received parameter value exceeds a timeout value. For example, the hub 15 may include a display 18 and a controller 35 configured to monitor and manage the received physiological data. For example, the controller 35 may include a receipt management module 23, which is software stored in memory 21 and executable on the processor 19 to track the time since the last received parameter value. The receipt management module 23 may also be configured to generate an alert and/or prompt the wireless physiological sensor 3 if the timeout value, or threshold period of time, is exceeded. Thereby, the hub 15 or other receiving device can check on a non-transmitting sensor 3 and determine if the lack of transmitted parameter values is due to consistency of the physiological data being recorded or due to other failure or other loss of the sensor 3.

Figure 3:
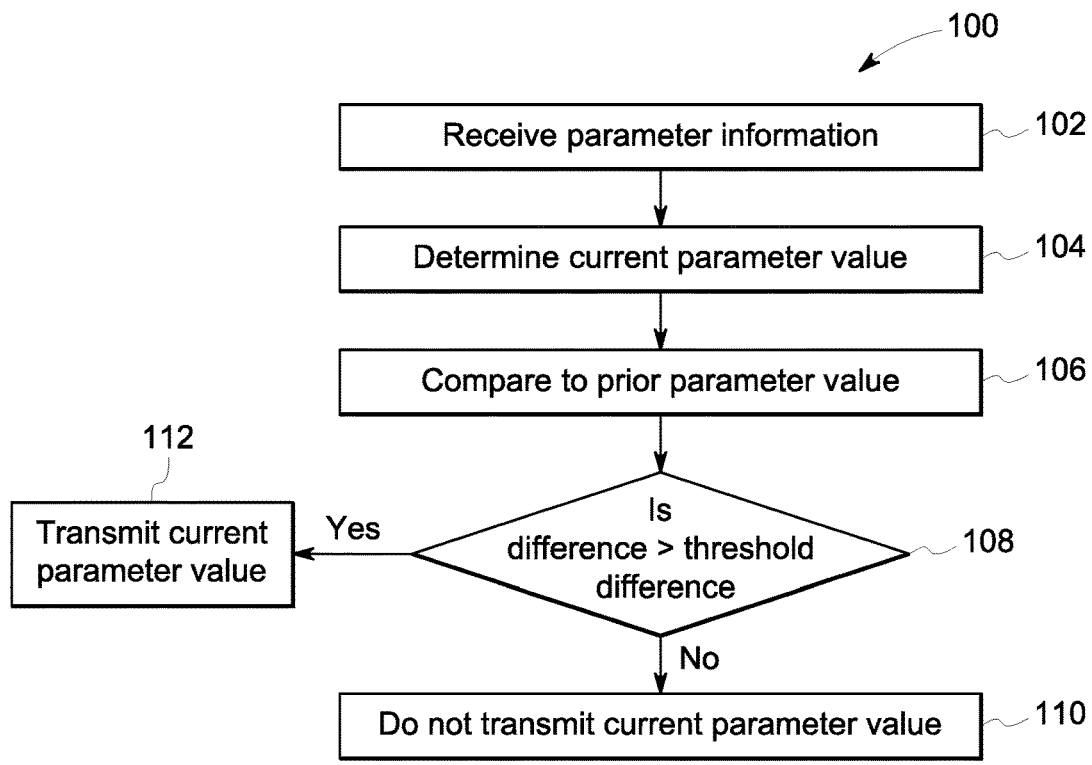
FIGS. 3-6 are flow charts demonstrating patient monitoring methods according to the present disclosure.

FIGS. 3-6 depict embodiments of patient physiological monitoring methods 100 in accordance with the present disclosure. In FIG. 3, physiological parameter information is received at step 102 and a current parameter value is determined at step 104 based on the physiological parameter information. For example, the current parameter value may be a discrete value describing the physiological parameter of the patient and based on the physiological parameter information, such as a heart rate, respiration rate, SpO2, temperature, etc. The current parameter value has been compared to a prior parameter value at step 106. In one embodiment, the prior parameter value is a last-transmitted parameter value, which is a previous parameter value that was most recently transmitted by the wireless physiological sensor 3. In other embodiments, the prior parameter value may be a recently determined parameter value by the wireless sensor 3—i.e., the previous "current parameter value" determined by the controller 135. In still other embodiments, the prior parameter value may be a filtered value, such as an average or mean of a predetermined previous values.

Instructions are then executed at step 108 to determine whether the current parameter value is redundant of the prior parameter value. For example, the current parameter value may be determined redundant of the prior parameter value if a difference between the current parameter value and the prior parameter value is less than a predetermined threshold difference. In one embodiment, the predetermined threshold difference may be a based on a resolution of the sensor 3 and/or sensing element 9. To provide one example with respect to a wireless temperature sensor 3d having a temperature sensing element 9d with a resolution of 0.1° C., the threshold difference may be 0.05° C. Thus, a temperature measuring within 0.05° C. of the prior parameter value, or prior temperature measurement, will be considered redundant. Thus, in this example, the threshold difference is approximately half of the sensor resolution value. In other embodiments, the threshold difference may be a different proportional value with respect to the sensor resolution. Alternatively or additionally, the predetermined threshold difference for determining redundancy may be based on other parameters, such as normal physiological variability or other factors. To provide one example regarding heart rate, a threshold difference for redundancy of a heartrate parameter value may be one beat per minute. An exemplary difference for determining redundancy of parameter values for respiration rate may be one breath per minute, to provide just one example. To provide one example of a predetermined threshold difference for assessing redundancy of SpO2 parameter values is 1%.

If the current parameter value is considered redundant at step 108, then the current parameter value is not transmitted as represented at step 110. If, on the other hand, the parameter value is not redundant—e.g., the difference between the current parameter value and the prior parameter value exceeds the threshold difference—then the current parameter value is transmitted at step 112.

Figure 4:
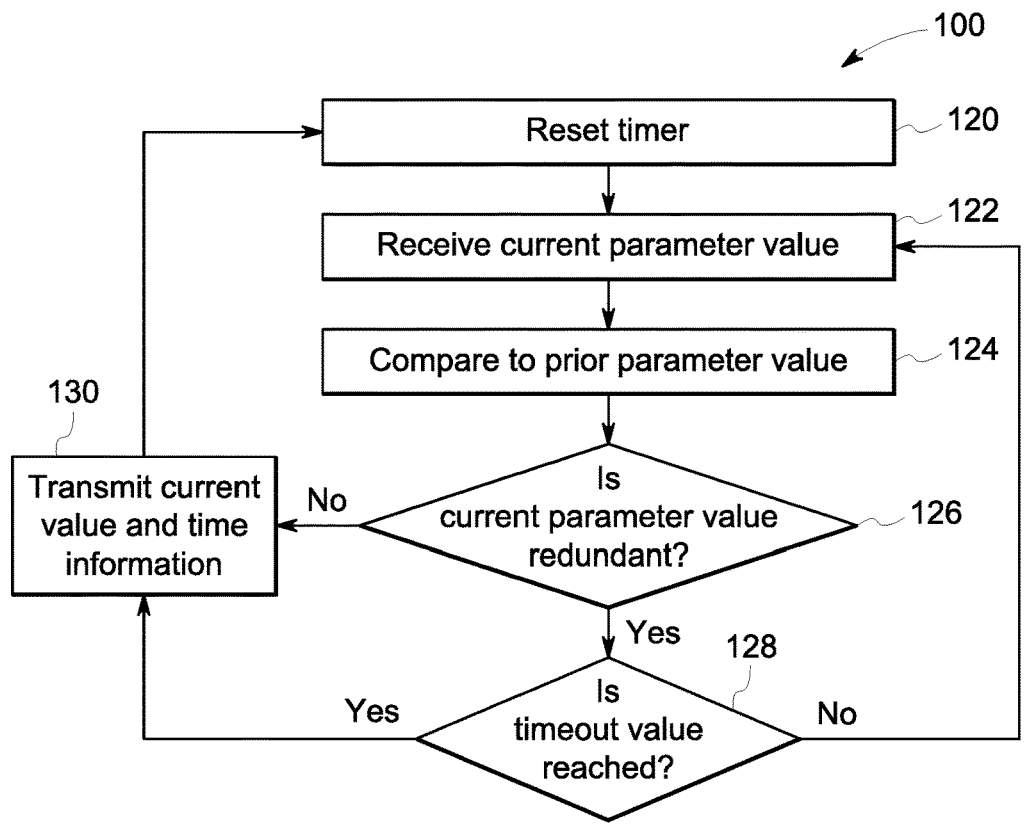

FIG. 4 depicts another embodiment of a patient monitoring method 100. A timer is started at step 120 and a current parameter value is received at step 122. The current parameter value is compared to a prior parameter value at step 124, as is described above. Instructions are executed at step 126 to determine whether the current parameter value is redundant of the prior parameter value, such as whether a threshold difference between the parameter values exists. If the current parameter value is not redundant, then instructions are executed at step 128 to determine whether a timeout value has been reached. Namely, it is determined whether a threshold amount of time has passed since the last parameter value was transmitted by the sensor 3. If the timeout value has not been reached, then the controller continues to determine new current parameter values and assess redundancy. Once the timeout value is reached, then the current parameter value is transmitted at step 130. In certain embodiments, time information may also be transmitted, such as the time that the current parameter value is determined and/or transmitted by the sensor 3. Alternatively or additionally, the time information may include a period of time between parameter value transmission by the sensor. Once the parameter value is transmitted, the timer is reset and the process starts again.

Figure 5:
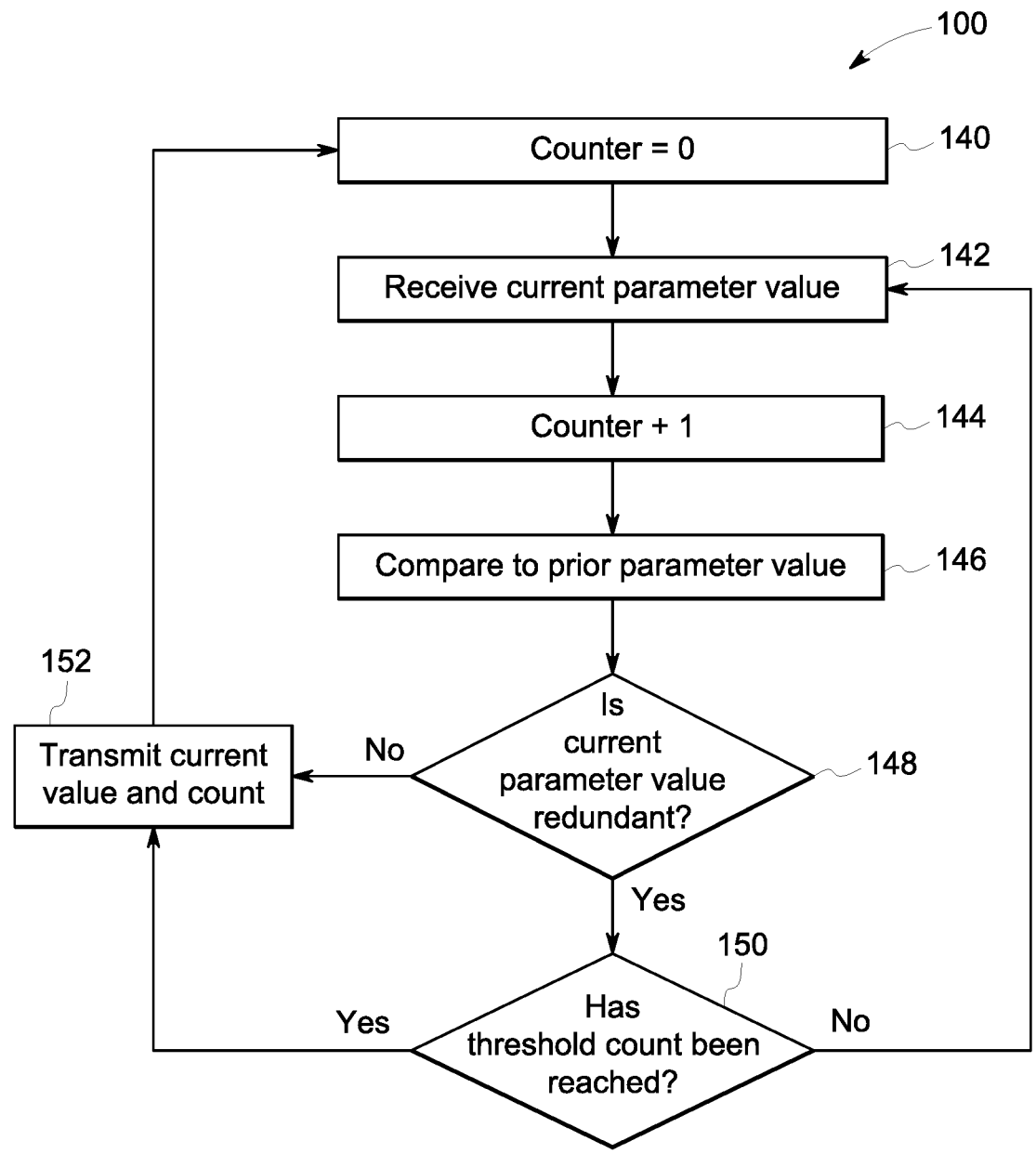

FIG. 5 demonstrates another embodiment where the sensor monitors non-transmission by counting a number of untransmitted redundant parameter values. The counter is set to zero at step 140 and the current parameter value is received at step 142. The counter is incremented by one at step 144. The current parameter value is compared to the prior parameter value at step 146. If the current parameter value is redundant of the prior parameter value, as determined at step 148, then instructions are executed at step 150 to determine whether a threshold number of untransmitted values has been reached—namely, whether the count exceeds a threshold. If not, then the sensor continues without transmitting the current parameter value. If the threshold count has been reached at step 150, and thus a threshold number of untransmitted values has been reached, the sensor transmits the current parameter value at step 152. In certain embodiments, the sensor 3 may also transmit the count value indicating the number of redundant parameter values not transmitted.

Figure 6:
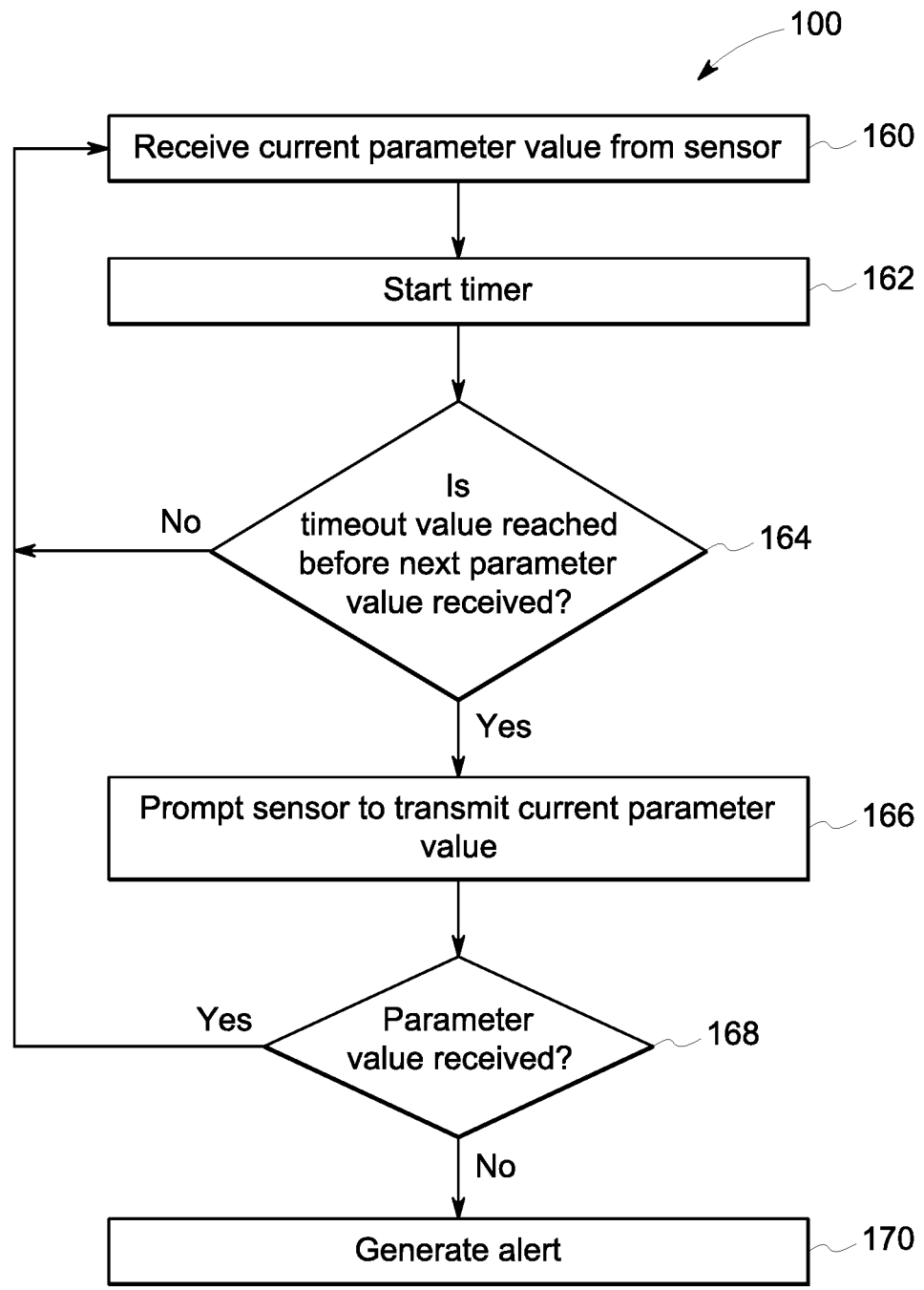

In certain embodiments, the hub 15—such as a patient monitor, the host network 30, or another receiving device—may be configured to track a period of time since the last received parameter value to ensure proper operation of the sensor 3. As shown in FIG. 6, the patient monitoring method 100 may include such steps. When a current parameter value is received from a sensor, as represented at step 160, a timer is started step 162. Instructions are executed at step 164 to determine whether a timeout value is reached prior to the next parameter value being received. If the next parameter value is received prior to the timeout value being reached, then there is no issue. However, if the timeout value is reached before the next parameter value is received, then the receiving device may execute steps to determine whether the sensor 3 is active and may generate an alert if no response is received from the sensor. In the example, the receiving device, such as the hub 15, prompts the sensor to transmit the current parameter value at step 166. For example, the hub 15 may wirelessly transmit a message to the sensor 3 instructing transmission. If the parameter value is received at step 168, then the issue may be resolved with no alert or event generation. However, if the parameter value is not received, an alert may be generated at step 170. For example, the alert may include an audio and/or visual alert by the user interface of the hub 15 or host network 30. For example, a missing sensor may be indicated on the display 18 indicating which wireless physiological sensor 3a-3d is not responding or transmitting. Similarly, an audio alert, such as an alarm, may be generated.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A wireless patient monitoring system comprising:
   at least one wireless physiological sensor having:
      a sensing element that senses physiological parameter information from a patient;
      a sensor controller configured to:
         determine a current parameter value based on the physiological parameter information;
         compare the current parameter value to a prior parameter value to determine if the current parameter value is redundant of the prior parameter value;
         if the current parameter value is not redundant of the prior parameter value, control a wireless transmitter to wirelessly transmit the current parameter value;
         if the current parameter value is redundant of the prior parameter value, not transmit the current parameter value;

wherein the current parameter value is determined to be redundant if a difference between the current parameter value and the prior parameter value is less than a predetermined threshold difference;

track a number of redundant parameter values not transmitted;

when the number of redundant parameter values not transmitted reaches a threshold number and/or when the current parameter value is not redundant of the prior parameter value and/or when a period of time since a last transmitted parameter value exceeds a timeout value, transmit the current parameter value and the number of redundant parameter values not transmitted without transmitting the redundant parameter values; and a patient monitor configured to receive the current parameter value from the wireless physiological sensor and assess a physiological condition of the patient based on the last transmitted parameter value for up to the timeout value.

2. The system of claim 1, wherein the sensor controller is configured to automatically transmit the current parameter value when the number of redundant parameter values not transmitted reaches the threshold number.

3. The method of claim 1, wherein the sensor controller is configured to, when the current parameter value is not redundant of the prior parameter value, transmit the number of redundant parameter values not transmitted with the nonredundant current parameter value without transmitting the redundant parameter values.

4. The system of claim 1, wherein the sensor controller is configured to track the period of time since the last transmitted parameter value and to automatically transmit the current parameter value when the period of time since the last transmitted parameter value exceeds the timeout value.

5. The system of claim 1, wherein the prior parameter value is the last transmitted parameter value by the wireless physiological sensor.

6. The system of claim 1, wherein the prior parameter value is a most recently determined parameter value by the wireless physiological sensor.

7. The system of claim 6, wherein the current parameter value and the prior parameter value are both one of a temperature, a heart rate, a respiration rate, and an $SpO_2$.

8. The system of claim 1, wherein the current parameter value and the prior parameter value are discrete values describing the physiological parameter information of the patient.

9. The system of claim 1, wherein the patient monitor is configured to track the period of time since a last received parameter value and, if the period of time since the last received parameter value exceeds the timeout value, to prompt the wireless physiological sensor to transmit the current parameter value.

10. The system of claim 1, wherein the patient monitor is configured to track the period of time since a last received parameter value and to generate an alert if the period of time since the last received parameter value exceeds the timeout value.

11. The system of claim 1, wherein the predetermined threshold difference is based on a resolution of the sensing element.

12. A method of patient physiological monitoring, the method comprising:

sensing physiological parameter information from a patient with a sensing element in a wireless physiological sensor;

at the wireless physiological sensor:

determining a current parameter value based on the physiological parameter information;

comparing the current parameter value to a prior parameter value to determine if the current parameter value is redundant of the prior parameter value, including determining that the current parameter value is redundant of the prior parameter value when a difference between the current parameter value and the prior parameter value is less than a predetermined threshold difference;

if the current parameter value is not redundant of the prior parameter value, operating a wireless transmitter to wirelessly transmit the current parameter value;

if the current parameter value is redundant of the prior parameter value, not transmitting the current parameter value;

tracking a number of redundant parameter values not transmitted;

if the number of redundant parameter values not transmitted reaches a threshold number and/or if the current parameter value is not redundant of the prior parameter value and/or if a period of time since a last transmitted parameter value exceeds a timeout value, transmitting the current parameter value and the number of redundant parameter values not transmitted without transmitting the redundant parameter values; and at a patient monitor configured to receive the current parameter value from the wireless physiological sensor:

assessing a physiological condition of the patient based on the prior parameter value for up to the timeout value or until the current parameter value is received from the wireless sensor.

13. The method of claim 12, further comprising tracking the number of redundant parameter values not transmitted and automatically transmitting the current parameter value when the number of redundant parameter values not transmitted reaches the threshold number.

14. The method of claim 12, further comprising tracking the number of redundant parameter values not transmitted and, if the current parameter value is not redundant of the prior parameter value, transmitting the number of redundant parameter values not transmitted with the nonredundant current parameter value.

15. The method of claim 12, further comprising tracking the period of time since a last transmitted parameter value and automatically transmitting the current parameter value when the period of time since the last transmitted parameter value exceeds the timeout value.

16. The method of claim 12, wherein the prior parameter value is the last transmitted parameter value by the wireless physiological sensor.

17. The method of claim 12, wherein the predetermined threshold difference is based on a resolution of the sensing element.

18. A wireless patient monitoring system comprising:

at least one wireless physiological sensor having:

a sensing element that senses physiological parameter information from a patient;

a sensor controller configured to:

determine a current parameter value based on the physiological parameter information;

compare the current parameter value to a prior parameter value to determine if the current parameter value is redundant of the prior parameter value;

if the current parameter value is redundant of the prior parameter value, not transmit the current parameter value and track a number of redundant parameter values not transmitted;

if the current parameter value is not redundant of the prior parameter value, control a wireless transmitter to wirelessly transmit the current parameter value and transmit the number of redundant parameter values not transmitted with the nonredundant current parameter value without transmitting the redundant parameter values; and wherein the current parameter value is determined to be redundant if a difference between the current parameter value and the prior parameter value is less than a predetermined threshold difference.

\* \* \* \* \*